US012788599B2

(12) United States Patent
Vancheri

(10) Patent No.: US 12,788,599 B2
(45) Date of Patent: Nov. 10, 2026

(54) STENT GRAFT CRIMPING DEVICE AND METHOD OF USE

(71) Applicant: Bolton Medical, Inc., Sunrise, FL (US)

(72) Inventor: Bryan Vancheri, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 315 days.

(21) Appl. No.: 18/741,192

(22) Filed: Jun. 12, 2024

(65) Prior Publication Data

US 2024/0325179 A1 Oct. 3, 2024

Related U.S. Application Data

(63) Continuation of application No. PCT/US2022/052968, filed on Dec. 15, 2022.

(60) Provisional application No. 63/290,344, filed on Dec. 16, 2021.

(51) Int. Cl.
*A61F 2/95* (2013.01)

(52) U.S. Cl.
CPC .................................. *A61F 2/9522* (2020.05)

(58) Field of Classification Search
CPC .......... A61F 2/95; A61F 2/9522; A61F 2/958; A61F 2/2418; A61F 2/82; A61F 2/07; A61F 2/2436; A61F 2/2427; A61F 2/9524; A61F 2/243; A61F 2/2466; A61F 2/24; A61F 2/92
See application file for complete search history.

(56) References Cited

U.S. PATENT DOCUMENTS 5,836,952 A * 11/1998 Davis .................... A61F 2/9526 606/1
6,024,737 A * 2/2000 Morales .................. A61F 2/958 606/1
6,125,523 A * 10/2000 Brown .................... A61F 2/958 606/1
6,141,855 A * 11/2000 Morales .................. A61F 2/958 606/1

(Continued)

FOREIGN PATENT DOCUMENTS

WO WO-2023/114371 A2 6/2023
WO WO-2023/114371 A3 7/2023
WO WO-2025207668 A1 * 10/2025 ........... A61F 2/2433

OTHER PUBLICATIONS

International Search Report and Written Opinion for International Application No. PCT/US2022/052968 dated Apr. 3, 2023.

(Continued)

*Primary Examiner* — Seema Mathew
(74) *Attorney, Agent, or Firm* — Stephen J. Kenny; Emily H. Yasharpour; Foley Hoag LLP

(57) ABSTRACT

A stent graft crimping device for radially constricting a stent graft includes a rigid cylinder defining a slot extending parallel to a longitudinal axis of a flexible sheet having a straight edge and a second edge and extending within the rigid cylinder to define a pocket. In a method of use, a stent graft can be positioned within the pocket and radially constricted by pulling on the second edge of the flexible sheet while the straight edge, having a raised component, remains at the slot defined by the rigid cylinder. The stent graft crimping device can be employed independently or as a system in combination with components of a stent graft delivery device.

20 Claims, 8 Drawing Sheets

(56) References Cited

U.S. PATENT DOCUMENTS

| | | | | |
|---|---|---|---|---|
| 7,389,670 | B1 * | 6/2008 | Kokish | A61F 2/95 72/402 |
| 8,308,792 | B2 * | 11/2012 | Ellsworth | A61F 2/82 623/1.11 |
| 10,322,020 | B2 * | 6/2019 | Lam | A61F 2/82 |
| 2004/0148007 | A1 | 7/2004 | Jackson et al. | |
| 2009/0228096 | A1 * | 9/2009 | Shifrin | A61B 17/072 623/1.36 |
| 2011/0295361 | A1 * | 12/2011 | Claiborne, III | A61F 2/2418 623/2.11 |
| 2013/0152658 | A1 * | 6/2013 | Davis | A61F 2/95 72/402 |
| 2013/0218139 | A1 * | 8/2013 | Fargahi | A61F 2/844 606/1 |
| 2015/0088240 | A1 * | 3/2015 | Lam | A61F 2/958 156/196 |
| 2018/0344490 | A1 * | 12/2018 | Fox | A61F 2/9524 |
| 2019/0091050 | A1 * | 3/2019 | Walsh | A61F 2/95 |
| 2019/0133798 | A1 * | 5/2019 | Gong | B25B 27/146 |
| 2021/0169646 | A1 * | 6/2021 | Taft | A61F 2/2418 |
| 2022/0008235 | A1 * | 1/2022 | Risch | A61F 2/9522 |
| 2024/0225867 | A1 * | 7/2024 | Saar | A61F 2/95 |
| 2024/0325179 | A1 * | 10/2024 | Vancheri | A61F 2/9522 |
| 2025/0009536 | A1 * | 1/2025 | Mitchell | A61F 2/9524 |
| 2025/0360006 | A1 * | 11/2025 | Eubanks | A61F 2/856 |

OTHER PUBLICATIONS

Extended European Search Report for EP Application No. 25209371.1 dated Feb. 3, 2026.

* cited by examiner

STENT GRAFT CRIMPING DEVICE AND METHOD OF USE

CROSS-REFERENCE TO RELATED APPLICATION

This application is a Continuation of and claims the benefit of priority under 35 USC 120 to International Patent Application No. PCT/US22/52968 filed Dec. 15, 2022, which claims the benefit of U.S. Provisional Patent Application No. 63/290,344, filed Dec. 16, 2021, the entire contents of which are incorporated herein by reference.

BACKGROUND OF THE INVENTION

Demonstration of stent graft delivery devices typically entails release of radially constricted, or "crimped," stent grafts that have previously been loaded within one or more delivery or "introducer" sheaths. Most stent grafts delivered by such devices are self-expanding and include a plurality of radially self-expanding stents, often fabricated of intermetallic or shape memory alloys. Once deployed in the course of demonstrating a surgical delivery device within which they had been packaged during assembly and fabrication, self-expanding stent graft typically are very difficult to reload by hand.

Known devices for loading surgical stent graft prostheses into surgical delivery devices, such as "iris crimpers," are complex, heavy, expensive, and too large for transport by personnel responsible for sales and marketing at locations remote from the place of their manufacture.

Therefore, a need exists for a device, system, and method of loading stent grafts into surgical delivery devices in the field.

SUMMARY OF THE INVENTION

The invention generally is directed to a stent graft crimping device and system for radially constricting a stent graft, and a method of loading a stent graft into a stent graft delivery device.

In one embodiment, the invention is a stent graft crimping device for radially constricting the stent graft that includes a rigid cylinder and a flexible sheet. The rigid cylinder has an outside surface and an inside surface, and defines a lumen and a slot extending parallel to a longitudinal axis of the rigid cylinder. The flexible sheet has a straight edge, a raised component at the straight edge, and a second edge opposite the straight edge. The raised component and the straight edge are parallel to and adjacent to the longitudinal slot at the outside surface of the rigid cylinder. The flexible sheet extends from the straight edge and through the slot into the lumen of the rigid cylinder, and from the lumen through the longitudinal slot to the second edge of the outside surface of the rigid cylinder, thereby defining a pocket of the flexible sheet within the lumen of the rigid cylinder.

In another embodiment, the invention is a stent graft loading system that includes a rigid cylinder, a flexible sheet, a guidewire catheter, an apex clasping component, and an apex clasping catheter. The rigid cylinder has an outside surface and an inside surface, and defines a lumen and a slot extending parallel to a longitudinal axis of the rigid cylinder. The flexible sheet has a straight edge, a raised component at the straight edge, and a second edge opposite the straight edge. The raised component and the straight edge are parallel to and adjacent to the longitudinal slot at the outside surface of the rigid cylinder. The flexible sheet extends from the straight edge and through the slot into the lumen of the rigid cylinder, and from the lumen through the longitudinal slot to the second edge at the outside surface of the rigid cylinder, thereby defining a pocket of the flexible sheet within the lumen of the rigid cylinder. The guidewire catheter extends through the pocket and has a distal end and a proximal end. The apex clasping component is fixed to the distal end of the guidewire catheter, and includes a distal clasping component at the distal end of the guidewire catheter and a proximal clasping component that is mateable to the distal clasping component and proximal to the distal clasping component. The apex clasping catheter is fixed to and extends proximally from the proximal clasping component of the apex clasping component.

In still another embodiment, the invention is a method of loading a stent graft into a stent graft delivery device and includes the step of loading the stent graft into a pocket defined by a flexible sheet having a straight edge and a second edge opposite the straight edge, wherein the straight edge has a raised component that extends parallel to and is adjacent a slot defined by a rigid cylinder, and extends parallel to a longitudinal axis of the rigid cylinder. The flexible sheet extends from the raised component of the straight edge through the slot and into a lumen defined by the rigid cylinder, and from within the lumen through the slot to the opposite edge of the flexible sheet outside the rigid cylinder to thereby define the pocket of the flexible sheet. The second edge of the flexible sheet is pulled away from the rigid cylinder, thereby reducing the volume of the pocket and radially constricting the stent graft and causing a longitudinal axis of the stent graft to move away from the longitudinal axis of the rigid cylinder and toward the slot of the rigid cylinder. The stent graft is directed along its longitudinal axis from the pocket into an independent radially constricting member while remaining radially constricted along its longitudinal axis.

This invention has many advantages. For example, the stent graft crimping device of the invention is simple to use and easily transportable. Further, the stent graft loading system and method of loading the stent graft into a stent graft delivery device of the invention can accommodate different types of stent grafts, such as those that employ longitudinal supports sewn into a fabric of the stent graft, including support bars, such as longitudinal support bars, and stent grafts that employ crown and clasping stents that must be mounted to apex clasping components of surgical stent graft delivery devices. Also, stent grafts that require external longitudinal sport, such as support wires that are fixed to and extend distally along other components of the surgical stent graft delivery device and are threaded through suture loops of the stent graft, also can be accommodated by the stent graft crimping device, system and method of use of the invention.

DETAILED DESCRIPTION OF THE INVENTION

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

A description of example embodiments follows.

The invention generally is directed to a stent graft crimping device and system for radially constricting a stent graft, and to a method of loading a stent graft into a stent graft delivery device.

When reference is made herein to an aortic prosthesis, such as a “stent graft,” “prosthesis,” “stent graft prosthesis,” “vascular prosthesis” or other prostheses to be delivered or implanted in a patient, the word “proximal” means that portion of the prosthesis or component of the prosthesis that is relatively close to the heart of the patient, while “distal” means that portion of the prosthesis or component of the prosthesis that is relatively far from the heart of the patient.

When, however, reference is made to a delivery system or a component of a delivery system employed to deliver, or implant, a prosthesis, the word, “proximal,” as that word is employed herein, means closer to the clinician using the delivery system. When reference is made to a delivery system where a component of the delivery system is “distal,” as that term is employed herein, means further away from the clinician using the delivery system.

For clarity, the word “proximate” means “close to,” as opposed to the meanings ascribed to “proximal” or “distal” described above with respect to either the prosthesis or delivery system.

Figure 1A:
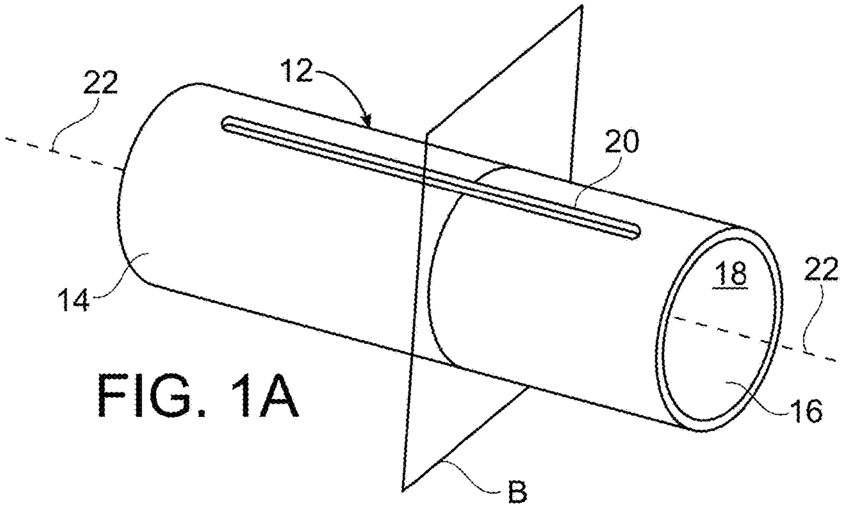
FIG. 1A is a perspective view of a rigid cylinder component of one embodiment of a stent graft crimping device of the invention.
Figure 1B:
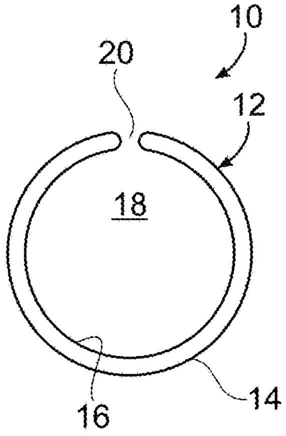
FIG. 1B is an end view of the rigid cylinder shown in FIG. 1A.
Figure 2A:
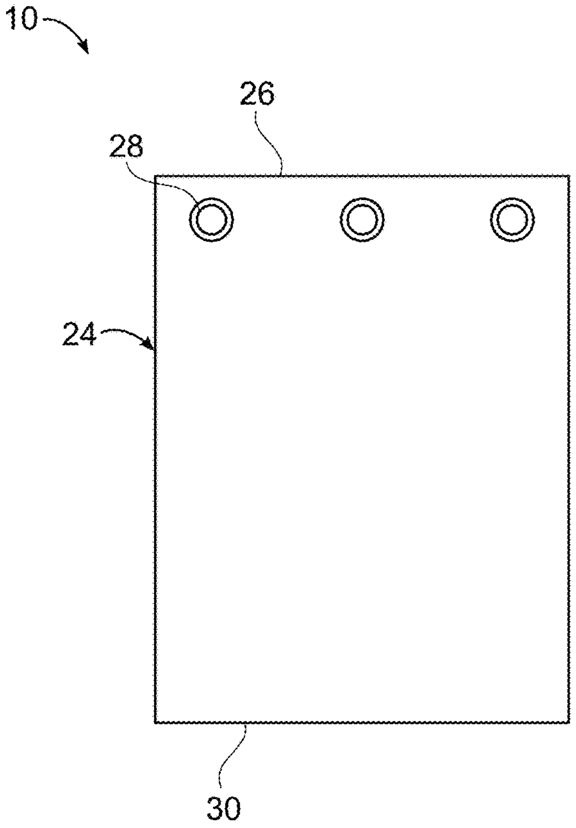
FIG. 2A is a plan view of a flexible sheet component of one embodiment of a stent graft crimping device of the invention.
Figure 2B:
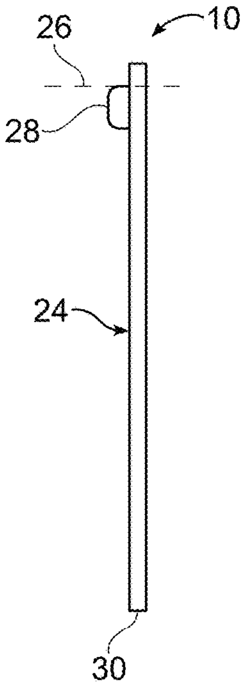
FIG. 2B is an edge view of the flexible sheet shown in FIG. 2A

Component parts of one embodiment of a stent graft crimping device 10 of the invention for radially constricting a stent graft is shown in FIGS. 1A, 1B, 2A, 2B. As can be seen in the perspective view of FIG. 1A, and the end view of FIG. 1B taken along plane B of FIG. 1A, stent graft crimping device 10 includes rigid cylinder 12 having outside surface 14 and inside surface 16, and defines lumen 18 and slot 20 extending parallel to longitudinal axis 22 of rigid cylinder 12. An example of a suitable material of construction of rigid cylinder 12 is clear acrylic. Flexible sheet 24, shown in plan and edge views in FIGS. 2A and 2B, respectively, has straight edge 26 and raised component 28 at straight edge 26, and second edge 30 that is opposite straight edge 26. An example of a suitable material of construction of flexible sheet is Teflon PTFE film having a thickness in a range of between about 0.010 inches and about 0.050 inches, in a preferred embodiment about 0.010 inches or 0.010 inches. Raised component 28 of flexible sheet 24 protrudes from at least one side of flexible sheet 24, as can be seen in FIG. 2B. Typically, raised component 28 is a nylon two-piece push-in rivet with a snap shank.

Figure 3A:
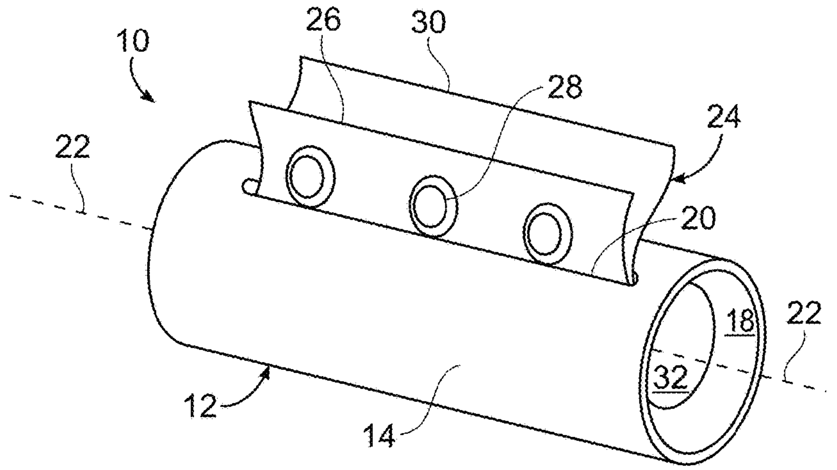
FIG. 3A is a perspective view of the assembled stent graft crimping device shown in FIGS. 1A, 1B, 2A, and 2B prior to radial constriction of a pocket defined by the flexible sheet of the stent graft crimping device of the invention.
Figure 3B:
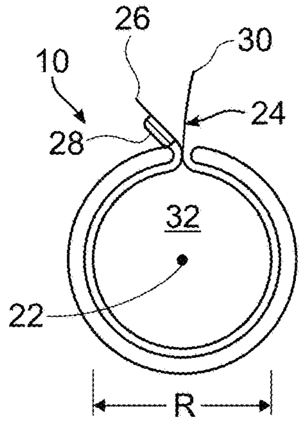
FIG. 3B is an end view of the stent graft crimping device of the invention shown in FIG. 3A.
Figure 4A:
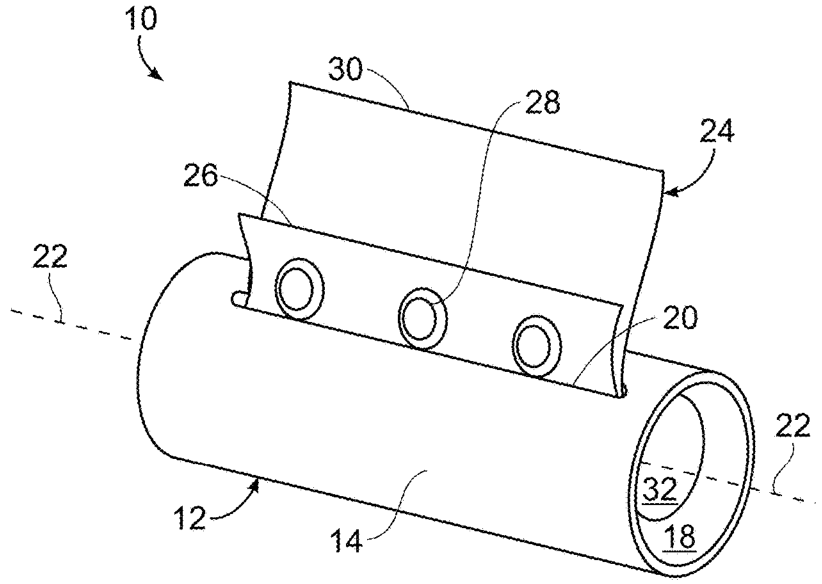
FIG. 4A is a perspective view of the stent graft crimping device of the invention shown in FIGS. 3A and 3B following radial constriction of the pocket defined by the flexible sheet.
Figure 4B:
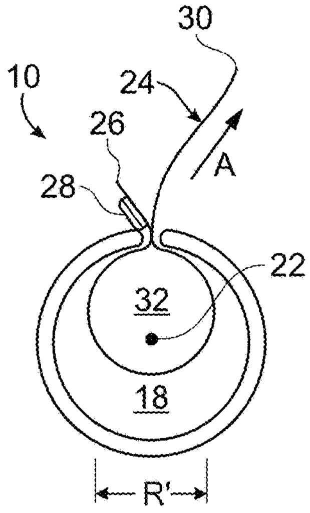
FIG. 4B is an end in view of the stent graft crimping device of the invention shown in FIG. 4A.

When assembled, as shown in FIGS. 3A and 3B, raised component 28 of straight edge 26 and second edge 30 are parallel to and adjacent to longitudinal slot 20 at outside surface 14 of rigid cylinder 12. Flexible sheet 24 extends from straight edge 26 and through longitudinal slot 20 into lumen 18 of rigid cylinder 12, and from lumen 18 through longitudinal slot 20 to second edge 30 at outside surface 14 of rigid cylinder 12, thereby defining pocket 32 of flexible sheet 24 within lumen 18 of rigid cylinder 12.

As demonstrated in the transition from FIGS. 3A and 3B to FIGS. 4A and 4B, pocket 32 defined by flexible sheet 24 reduces in radial diameter R of pocket 32 to reduced radial diameter R' by pulling second edge 30 in direction A away from longitudinal slot 20 of rigid cylinder 12, such as by hand. Raised component 28 of flexible sheet 24 prevents straight edge 26 from being pulled into lumen 18 of rigid cylinder 12, and friction between contacting surfaces at flexible sheet 24 at longitudinal slot 20 where flexible sheet 24 passes through longitudinal slot 20 can provide some resistance to expansion of pocket 32 once it has been radially constricted by pulling of second edge 30 of flexible sheet 24.

Figure 5A:
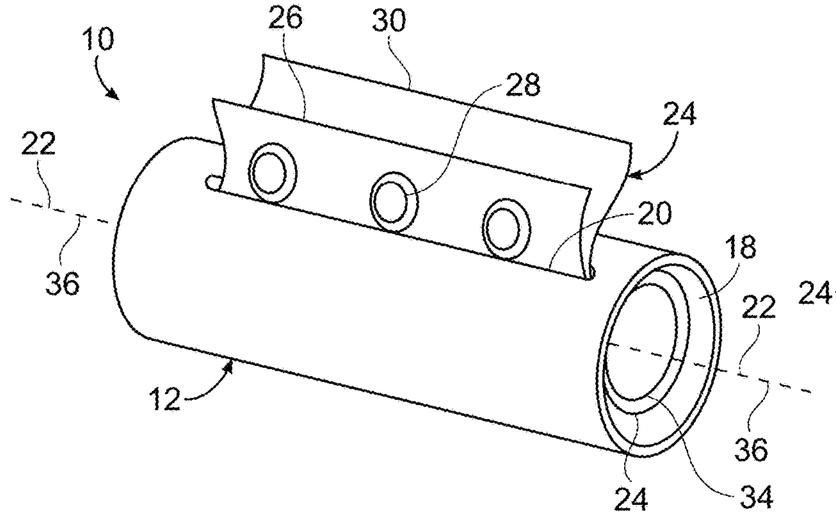
FIG. 5A is a perspective view of the stent graft crimping device shown in FIGS. 1A through 4B wherein a stent graft has been loaded into the pocket defined by the flexible sheet, but prior to radially constricting the stent graft by an embodiment of a method of the invention.
Figure 5B:
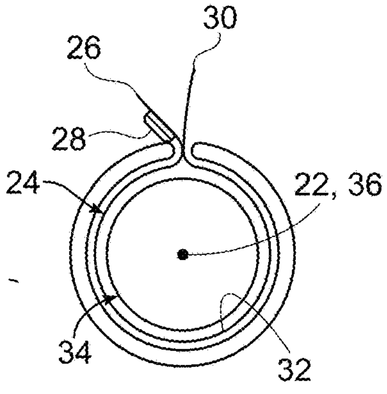
FIG. 5B is an end view of the stent graft crimping device and loaded stent graft prosthesis of FIG. 5A.
Figure 6A:
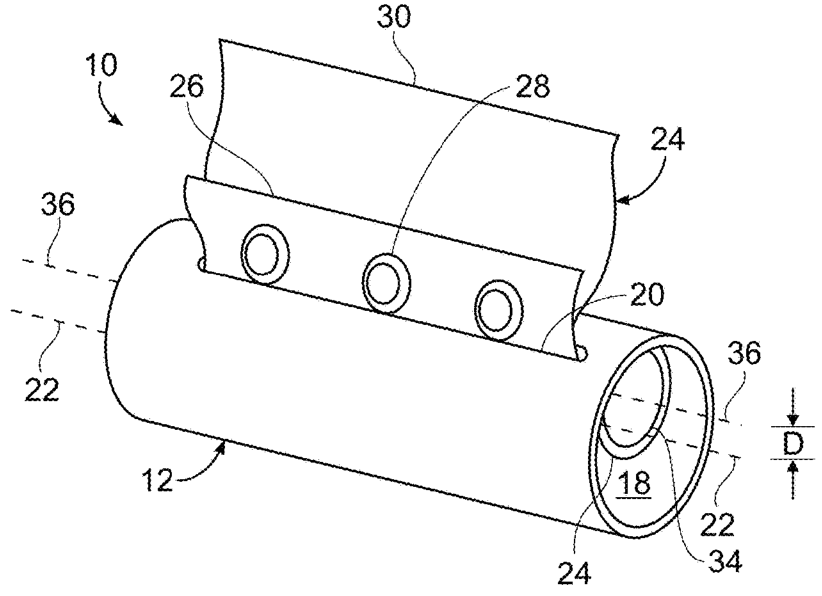
FIG. 6A is a perspective view of the stent graft crimping device shown in FIGS. 5A and 5B, but following radial constriction of the stent graft by the method of the invention.
Figure 6B:
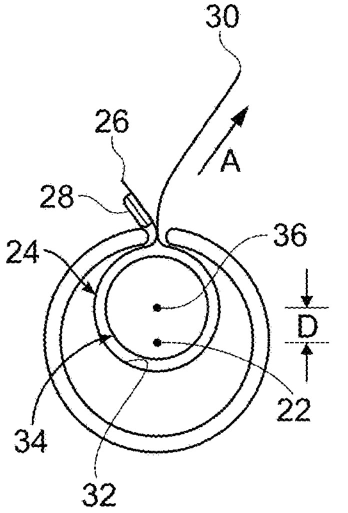
FIG. 6B is an end view of the stent graft crimping device shown in FIG. 6A.

FIGS. 5A and 5B, and 6A and 6B show the embodiment of the stent graft crimping device of the invention of FIGS. 1A-4B upon loading with radially self-expandable stent graft 34. As can be seen in FIG. 5B, radially self-expanding stent graft 34 is in a relatively relaxed state within pocket 32 defined by flexible sheet 24 within lumen of rigid cylinder 12 prior to radial constriction by the method of the invention. Longitudinal axis 22 of rigid cylinder 12 and longitudinal axis 36 of radially self-expandable stent graft 34 can coincide, as shown in FIG. 5B.

Upon pulling second edge 30 of flexible sheet 24 away from longitudinal slot 20 of rigid cylinder 12, as shown in the transition from FIG. 5A to FIG. 6A, radially self-expanding prosthesis 34 becomes radially constricted, as shown in the progression from FIG. 5B to FIG. 6B. As radially self-expanding stent graft 34 becomes radially constricted, longitudinal axis 36 of radially self-expanding stent graft 34 moves away from longitudinal axis 22 of rigid cylinder 12. In one instance, shown in FIGS. 5A and 5B, where longitudinal axes 22, 36 of rigid cylinder 12 and radially self-expanding stent graft 34, respectively, coincide, longitudinal axis 36 of radially self-expanding prosthesis 34 moves distance D from longitudinal axis 22 of rigid cylinder 12 during radial constriction caused by pulling second edge 30 away from longitudinal slot 20 of rigid cylinder 12.

Figure 7:
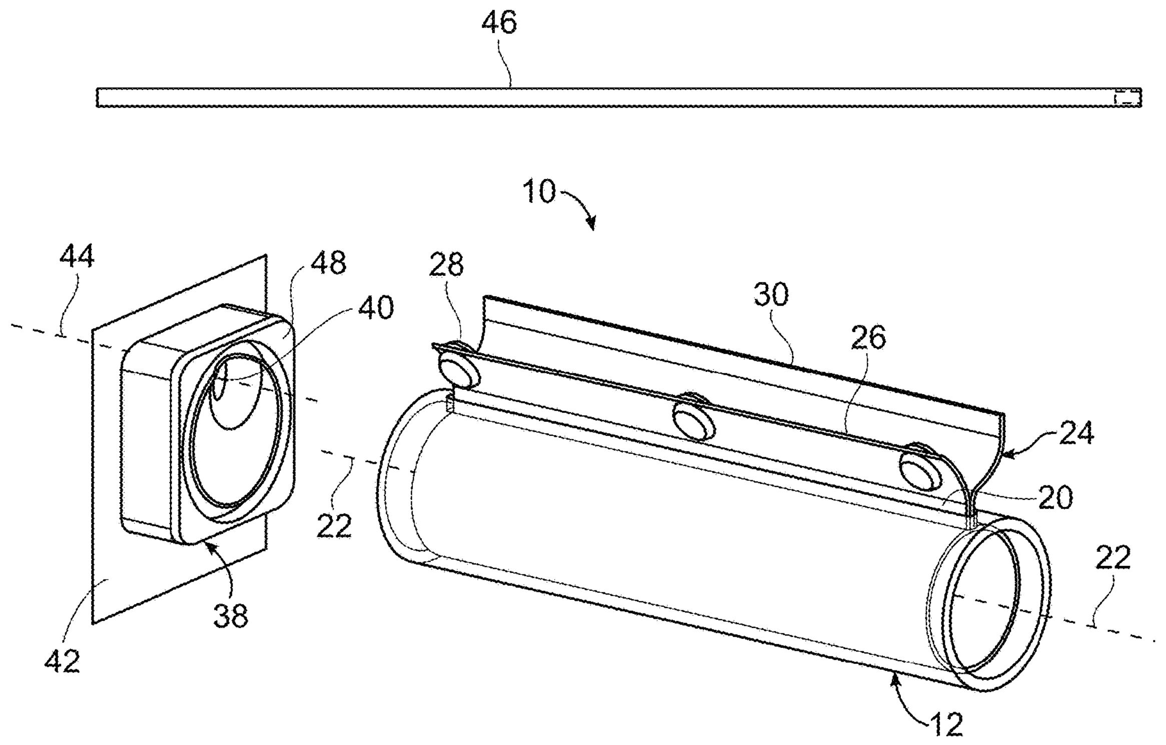
FIG. 7 is an exploded view, in perspective, of another embodiment of the stent graft crimping device of the invention, further including a loading block and a loading tube.
Figure 8:
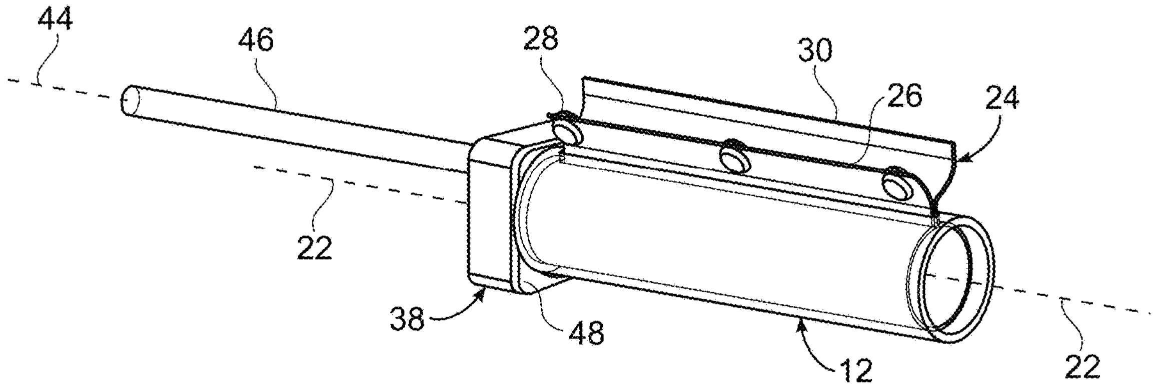
FIG. 8 is an assembled view of the stent graft crimping device of FIG. 7.

FIG. 7 is an exploded view of one specific embodiment of a stent graft crimping device of the invention, further including loading block 38 mateable to rigid cylinder 12. Loading block 38 typically is formed by 3D printing using an acrylonitrile butadiene styrene (ABS)-type material. Loading block 38 defines opening 40 in a plane 42 that is perpendicular to longitudinal axis 21 of rigid cylinder 12. Opening 40 defines center axis 44 that is parallel to longitudinal axis 22 of rigid cylinder 12, but spaced apart from longitudinal axis 22 of rigid cylinder 22. In one specific embodiment, loading tube 46 extends from opening 40 at loading block 38 opposite to portion 48 of loading block 38 that is mated with rigid cylinder 12, as shown in FIG. 8, by suitable means, such as by an interference fit. Loading tube 46 typically is matched by an interference fit with loading block 38 and is formed of clear PTFE tubing. Loading tube 46 can be an intermediate means, whereby radially compacted radially self-expandable prosthesis 34, once delivered to loading tube 46, is then sheathed by substitution of loading tube 46 with a secondary sheath of surgical delivery device (not shown).

Figure 9:
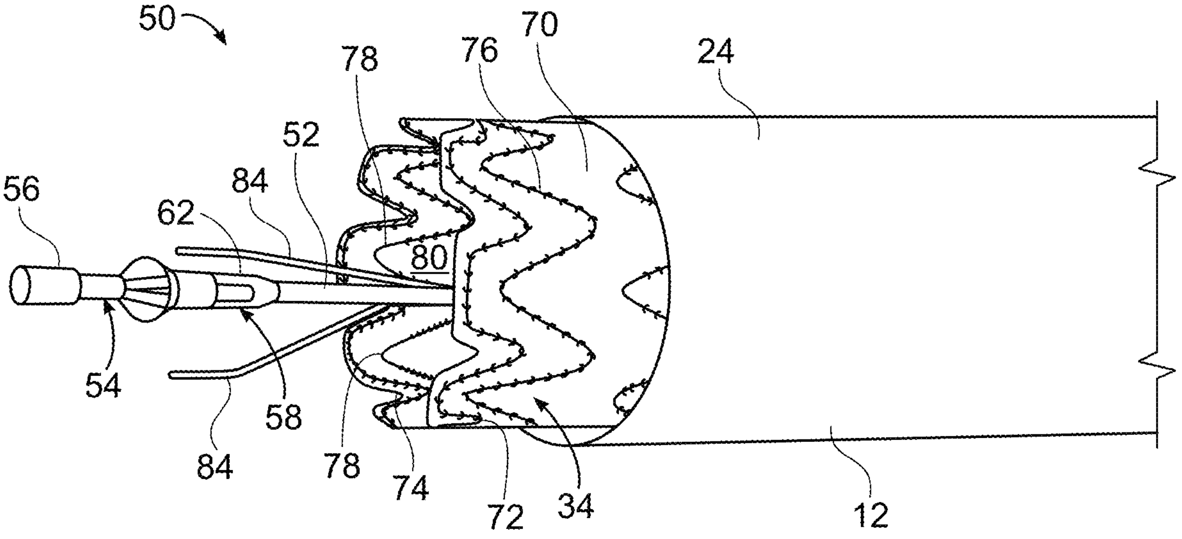
FIG. 9 is a detail of another embodiment of a stent graft loading system of the invention, showing a proximal end of a stent graft partially withdrawn from a rigid cylinder in order to mount a clasping stent of the stent graft onto an apex clasping component of the stent graft loading system, and sutures of the stent graft onto support wires of the stent graft loading system.
Figure 10:
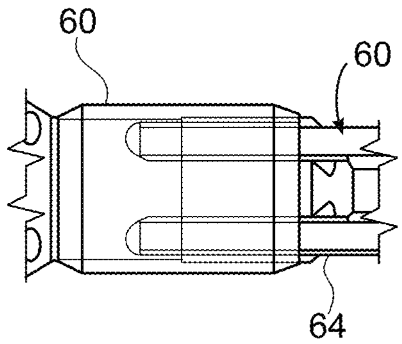
FIG. 10 is one embodiment of an apex clasping component of the stent graft loading system of FIG. 9 in a closed position.

In another embodiment of the invention, stent graft loading system 50 includes rigid cylinder 12 and flexible sheet 24, and also at least one component of a stent graft delivery device. As shown in FIG. 9, for example, stent graft loading system 50 includes, in addition to rigid cylinder 12 and flexible sheet 24, guidewire catheter (not shown) extending through apex clasping catheter 52. Guidewire catheter 54 has distal end 56 and a proximal end (not shown), and is part of a prosthesis delivery device employed by a surgeon or for demonstration by field personnel. Apex clasping component 58 of stent graft loading system 50 includes distal clasping component 60 that is fixed at distal end 56 of guidewire catheter 54. Proximal clasping component 62 of apex clasping component 58 includes tines 64 that extend distally from proximal clasping component 62. Apex clasping catheter 52 extends proximally from proximal clasping component 62 of apex clasping component 58. Proximal clasping component 62 is mateable to distal clasping component 60, as shown in FIG. 10. Examples of suitable clasping components can be found in U.S. Pat. Nos. 8,292,943 and 10,646,365, the entire teachings of which are incorporated by reference in their entirety.

Figure 11:
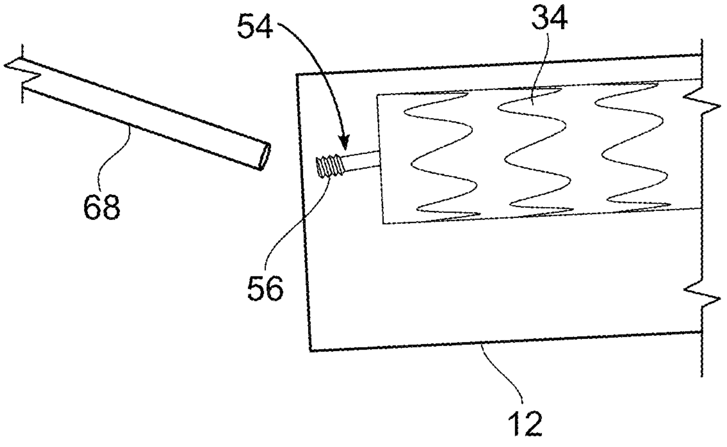
FIG. 11 is a perspective view of a loading rod of the stent graft loading system of FIG. 9 that is threadably fixable to a guidewire catheter of a stent graft delivery device suitable for use with the invention.
Figure 12:
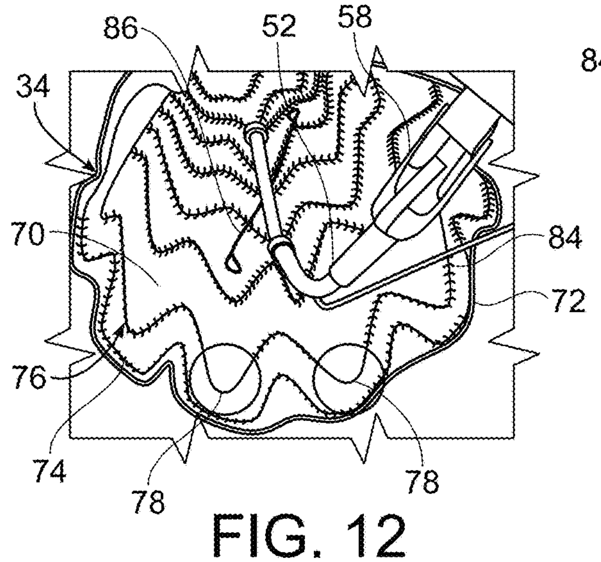
FIG. 12 is a perspective view of a stent graft suitable for use with the invention that includes a crown stent, and a clasping stent with bare proximal apices that can be captured by an apex clasping component, also shown in FIG. 12.

As can be seen in FIG. 11, in one specific embodiment, loading rod 68 is releasably fixable to distal end 56 of guidewire catheter 54, such as by threading onto threaded distal end 56 of guidewire catheter 54 prior to fully assembling the delivery device. Loading rod 68 typically is formed of stainless steel.

In one embodiment of stent graft loading system 50 of the invention, radially self-expandable stent graft 34 is within pocket 32 defined by flexible sheet 24, but can be partially withdrawn from pocket 32, as shown, for example, in FIG. 9, to allow axis to components of stent graft delivery system that are also components of the stent graft loading system 50 of the invention. Specifically, in one embodiment, radially self-expandable stent graft 34 includes luminal graft component 70 having proximal end 72 and distal end (not shown). As shown in FIG. 9, radially self-expandable stent graft 34 includes crown stent 74 fixed to proximal end 72 of luminal graft component 70. Crown stent 74 is proximal and adjacent to clasping stent 76. Clasping stent 76 includes at least one bare apex 78 that is exposed to lumen 80 of luminal graft component 70.

Figure 13:
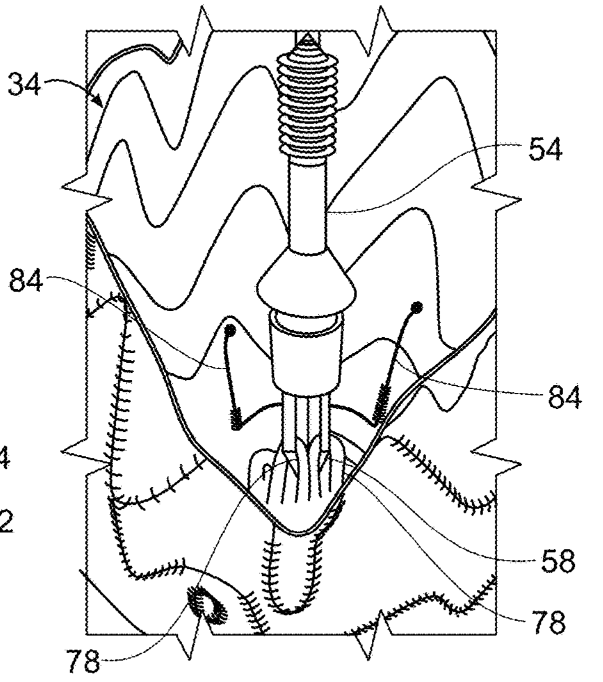
FIG. 13 is a perspective view of the stent graft of FIG. 12 following capture by the apex clasping component.

In the embodiment shown in FIGS. 9 through 13, proximal clasping component includes tines 64, or prongs, that extend distally from proximal clasping component 62 and are mateable with distal clasping component 60, whereby at least one bare proximal apex 78 of clasping stent 76 can be captured between tines 64 of proximal clasping component 62 and distal clasping component 60, as shown in FIG. 13, by distal movement of apex capture catheter 52 to move tines 64 of distal clasping component 60 through the at least one bare apex 78 of clasping stent 76 and into mating relation with distal apex clasping component 60 to thereby capture bare proximal apex 78. One bare apex is captured by each prong of proximal apex clasping component 62. The at least one bare proximal apex 78 can then be released by proximal movement of apex clasping catheter 52, to thereby move proximal clasping component 62 out of mating relation with distal clasping component 60.

Figure 14:
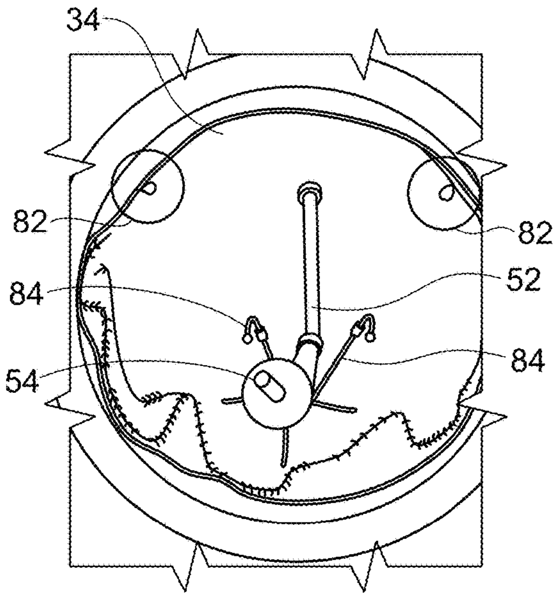
FIG. 14 is a perspective view of a stent graft that includes suture loops that are threadable by wire supports of a delivery device suitable for use with the stent graft loading system of the invention.
Figure 15:
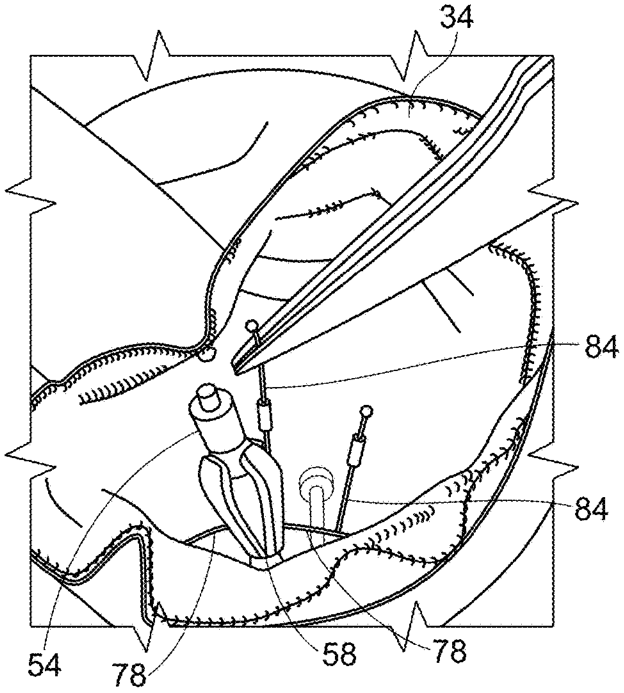
FIG. 15 is a perspective view of the stent graft of FIG. 14 while the suture loops are being threaded by the support wires that are components of this embodiment of the stent graft loading system of the invention.

In another embodiment, independently or in combination with any of the embodiments described above, radially self-expandable stent graft 34 includes at least one suture loop 82 at proximal end 72 of radially self-expandable stent graft 34 and within radially self-expandable stent graft 34, as shown in FIG. 14. In this embodiment, typically at least one support wire 84 is fixed to and extends distally from apex clasping catheter 52. The at least one support wire 84 is to be threaded through the at least one suture loop 82, as shown in FIG. 15.

Figure 16:
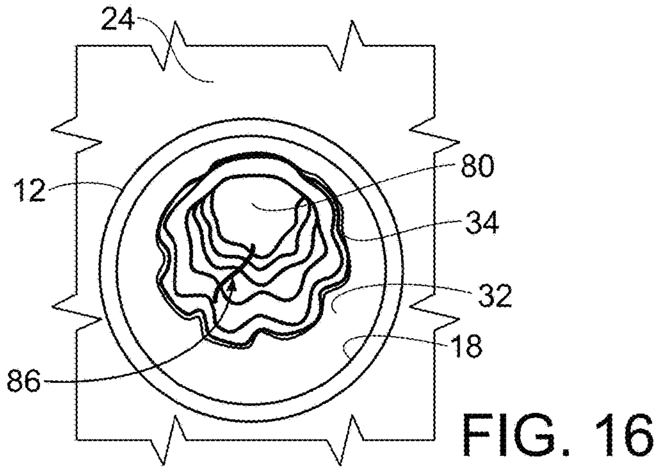
FIG. 16 is an end view of a stent graft of the invention that includes an S-bar support as loaded within a pocket defined by a flexible sheet of a stent graft crimping device of the invention.

In still another embodiment, taken separately or in combination with any of the other embodiments described herein, radially self-expandable stent graft 34 includes an S-bar support 86 secured to luminal graft component 70 of radially self-expandable stent graft 34, wherein S-bar support 86 is diametrically opposed to longitudinal slot 20 of rigid cylinder 12 when radially self-expandable stent graft 34 is loaded within pocket 32 defined by flexible sheet 24, as can be seen in FIG. 16.

Figure 17:
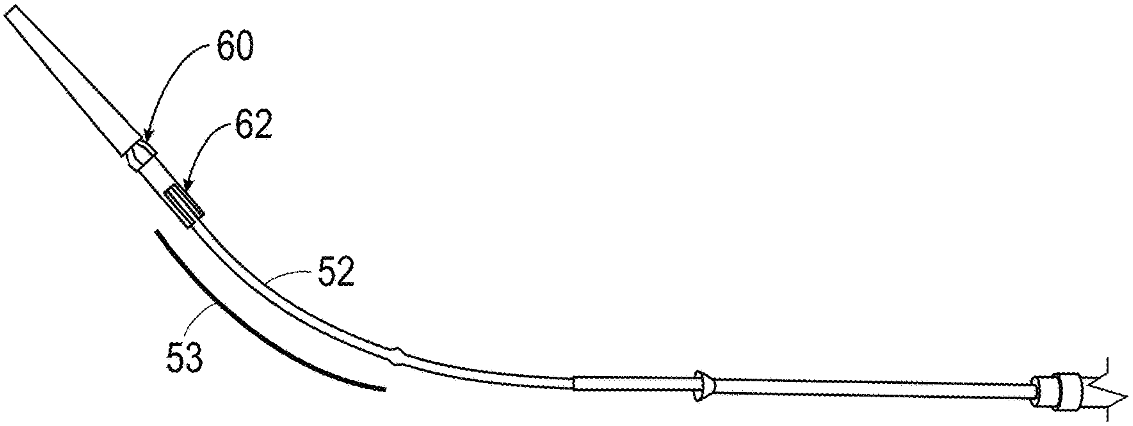
FIG. 17 is a side view of one embodiment of a stent graft delivery device that is suitable for use with the stent graft crimping device and stent graft loading system of the invention.

In one embodiment, taken separately or in combination with any of the other embodiments described herein, guidewire catheter 54 (shown, for example, in FIG. 9) is curved (as can be seen in FIG. 17). In one such embodiment, where stent graft includes support-bar 86 (also referred to as an "S-bar" and exemplified, for example in U.S. Pat. No. 8,292,943, the entire teachings of which are incorporated by reference). As described above, support bar 86 is at a superior position of curvature 53 of apex capture catheter 52, shown in FIG. 17, and to longitudinal slot 20 of rigid cylinder 12.

In another embodiment, the invention is a method of loading a stent graft, such as radially self-expandable stent graft 34, into a stent graft delivery device. In one embodiment of a method of the invention, the method includes loading a radially self-expandable stent graft 34 into pocket 32 defined by a flexible sheet 24 having straight edge 26 and second edge 30 opposite straight edge 26, wherein straight edge 26 has raised component 28 that extends parallel to and is adjacent to longitudinal slot 20 defined by rigid cylinder 12 and extending parallel to longitudinal axis 22 of rigid cylinder 12, flexible sheet 24 extending from raised component 28 of straight edge 26 through longitudinal slot 20 and into lumen 18 defined by rigid cylinder 12 and from within lumen 18 through longitudinal slot 20 of second edge 30 of flexible sheet 24 outside of rigid cylinder 12 to thereby define pocket 32 of flexible sheet 24.

Second edge 30 of flexible sheet 24 is pulled away from rigid cylinder 12, such as by hand, thereby reducing the volume of pocket 32 and radially constricting radially self-expandable stent graft 34, causing longitudinal axis 36 of radially self-expandable stent graft 34 to move away from longitudinal axis 22 of rigid cylinder 12 and toward longitudinal slot 22 of rigid cylinder 12, as described and shown above with reference to FIGS. 5A and 5B and 6A and 6B.

Figure 18:
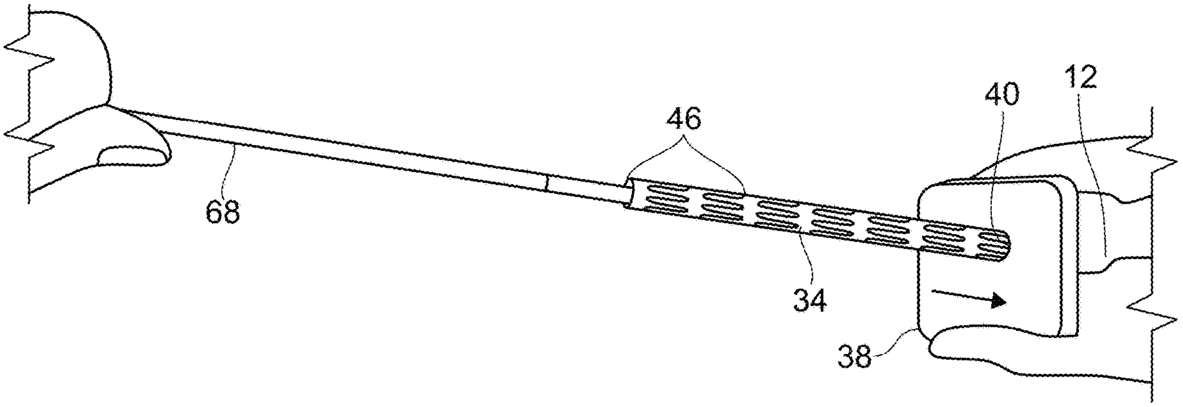
FIG. 18 is a perspective view of one embodiment of a method step of the invention including loading a radially constricted stent graft from rigid cylinder, through a loading block, and into a loading tube of one embodiment of the stent graft crimping device of the invention.

Radially self-expandable stent graft 34 is then directed, along its longitudinal axis 36 from pocket 32 into loading tube 46 while radially self-expandable stent graft 34 is in a radially constricted position. In one embodiment, radially self-expandable stent graft 34 is directed from pocket 32 into loading tube 46 through opening 40 of loading block 38 at one end of rigid cylinder 12, as shown in FIG. 18. Opening 40 defined by loading block 38 has a diameter less than that of pocket 32 prior to radially constricting pocket 32 and radially self-expandable stent graft 34, and wherein loading block 38 is beveled at the circumference of opening 40.

Figure 19:
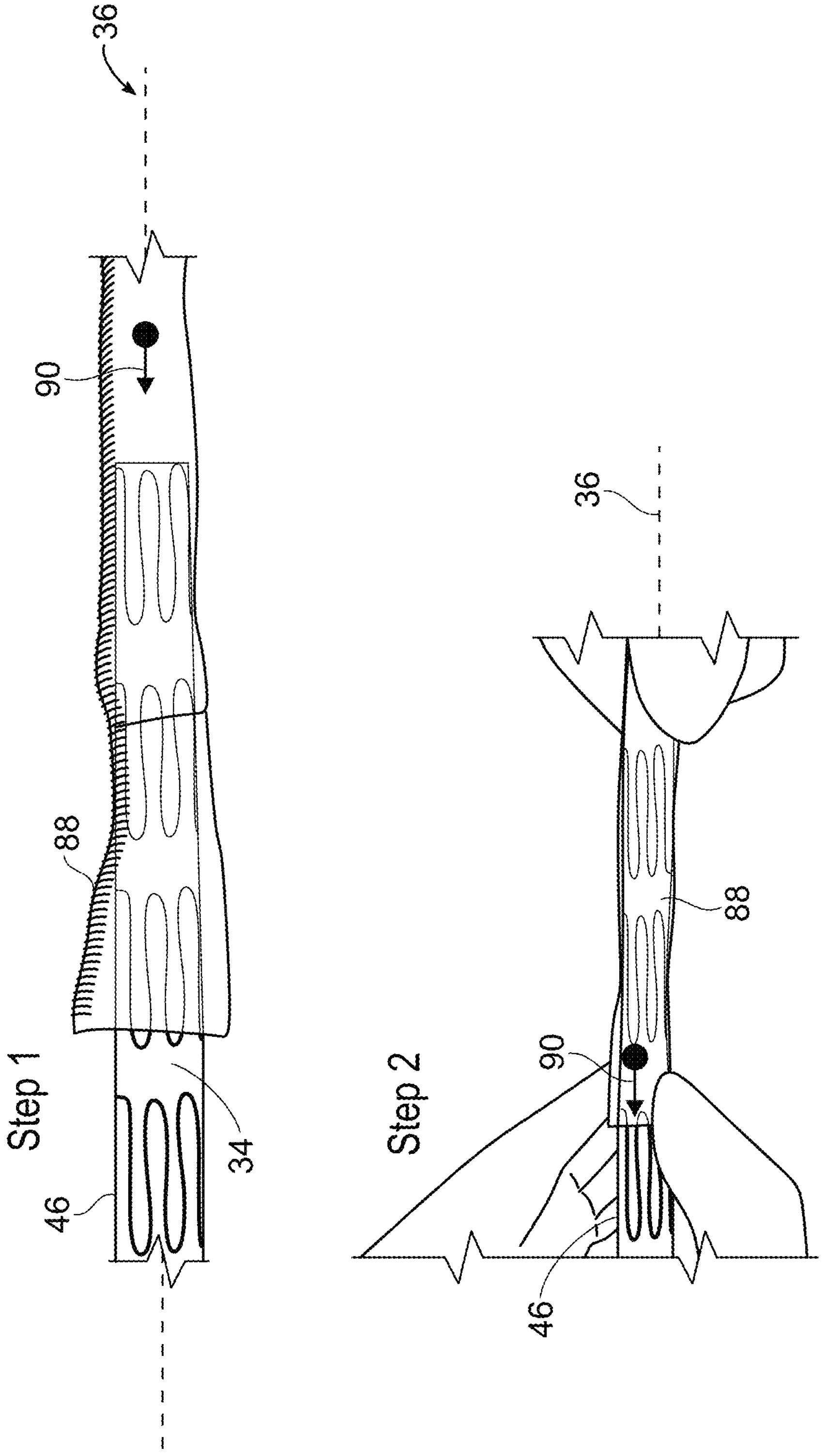
FIG. 19 is a perspective view of one embodiment of two additional method steps following that shown in FIG. 18, wherein the loading tube is substituted with a secondary sheath of a stent graft delivery device suitable for use with the stent graft crimping device of the invention.

Loading block 38, flexible sheet 24, and rigid cylinder 12 can then be removed, and loading tube 46 is then replaced by flexible sheath 88 of the stent graft delivery device along longitudinal axis 36 of radially self-expandable stent graft 34 while it is radially constricted, as can be seen in the transition from "Step 1" to "Step 2" of FIG. 19. More specifically, loading block 38, flexible sheath 24, and rigid cylinder 12 are displaced proximally toward the individual loading the stent graft delivery device over the outside diameter of a primary sheath of the system, proximally as indicated by arrow 90. Stent graft loading system 50, loading block 38, flexible sheath 24, and rigid cylinder 12 are moved away, but not removed from the delivery system until the stent graft is fully loaded into the stent graft delivery system.

In yet another embodiment, the method of the invention includes the step of clasping at least one proximal bare apex 78 of clasping stent 76 of radially self-expandable stent graft 34 to apex clasping component 58 of a stent graft delivery device prior to constricting radially self-expandable stent graft 34 within pocket 32 defined by flexible sheet 24 of stent graft crimping device 10 of the invention, as can be seen in FIG. 18.

In one such embodiment, the method further includes the step of removing clasping stent 76 of radially self-expandable stent graft 34 from pocket 32 before clamping proximal bare apex 78 of clasping stent 76 to apex clasping component 58 of the stent graft delivery device, and then redirecting clasping stent 76 back into pocket 32, as can be seen in FIG. 9.

In still another embodiment, the method of the invention includes threading at least one support wire 84 of the stent graft delivery device through suture loop 82 of radially self-expandable stent graft 34 prior to radially constricting radially self-expandable stent graft 34, as can be seen in FIGS. 14 and 15. In still another embodiment, the method further includes the step of applying a clamp to threaded suture loop 82 prior to radially constricting radially self-expandable stent graft 34.

Another embodiment of the method, which can be conducted in combination with any of the method steps described above, loading rod 68 is screw-loaded onto distal end 56 of guidewire catheter 54 of a stent graft delivery device, as can be seen in FIG. 11.

In yet another embodiment, when radially self-expandable stent graft 34 includes support bar 86, support bar 86 of radially self-expandable stent graft 34 is oriented during loading into pocket 32 radially opposite to longitudinal slot 20 of rigid cylinder 12, as can be seen in FIG. 16.

The teaching of all patents, published applications and references cited herein are incorporated by reference in their entirety. Suitable systems, delivery devices and components of systems, stent grafts as described in U.S. Pat. Nos. 7,763,063; 8,007,605; 8,062,345; 8,062,349; 8,070,790; 8,292,943 and 8,308,790, 8,740,963, 9,198,786, 9,320,631, 9,364,314, and 9,592,112, the relevant teachings of all of which are hereby incorporated by reference in their entirety, can be employed to deliver the aortic graft assembly of the invention by the method of the invention.

While example embodiments have been particularly shown and described, will be understood by those skilled in the art in various changes in form and details may be made therein without departing from the scope of the embodiments encompassed by the pendent claims.

What is claimed is:

1. A stent graft crimping device for radially constricting a stent graft, comprising;

a) a rigid cylinder having an outside surface and inside surface, and defining a lumen and a longitudinal slot extending parallel to a longitudinal axis of the rigid cylinder; and b) a flexible sheet having a straight edge, a raised component at the straight edge, and a second edge opposite the straight edge, the raised component and the straight edge being parallel to and adjacent to the longitudinal slot at the outside surface of the rigid cylinder, the flexible sheet extending from the straight edge and through the slot into the lumen of the rigid cylinder, and from the lumen through the longitudinal slot to the second edge at the outside surface of the rigid cylinder, thereby defining a pocket of the flexible sheet within the lumen of the rigid cylinder.

2. The stent graft crimping device of claim 1, further including a loading block that is mateable to the rigid cylinder and defines an opening in a plane that is perpendicular to the longitudinal axis of the rigid cylinder, the opening defining a center at an axis and parallel to the longitudinal axis of the rigid cylinder, but spaced apart from the longitudinal axis of the rigid cylinder, whereby radial constriction of a stent graft within the pocket defined by the flexible sheet consequent to pulling the second edge of the flexible sheet opposite the straight edge, will cause a longitudinal axis of the stent graft to align with the center of the opening defined by the block, the stent graft thereby being radially constricted and longitudinally moveable from the rigid cylinder through the opening and loaded into a loading tube.

3. A stent graft loading system, comprising:

a) a rigid cylinder having an outside surface and inside surface, and defining a lumen and a longitudinal slot extending parallel to a longitudinal axis of the rigid cylinder;

b) a flexible sheet having a straight edge, a raised component at the straight edge, and a second edge opposite the straight edge, the raised component and the straight edge being parallel to and adjacent to the longitudinal slot at the outside surface of the rigid cylinder, the flexible sheet extending from the straight edge and through the slot into the lumen of the rigid cylinder, and from the lumen through the longitudinal slot to the second edge at the outside surface of the rigid cylinder, thereby defining a pocket of the flexible sheet within the lumen of the rigid cylinder;

c) a guidewire catheter extending through the pocket, the catheter having a distal end and a proximal end;

d) an apex clasping component fixed to the distal end of the guidewire catheter, the apex capture component including a distal clasping component at the distal end of the guidewire catheter and a proximal clasping component that is mateable to the distal clasping component and proximal to the distal clasping component; and e) an apex clasping catheter fixed to and extending proximally from the proximal clasping component of the apex clasping component.

4. The stent graft loading system of claim 3, further including a loading rod that is releasably fixable to the distal end of the guidewire catheter.

5. The stent graft loading system of claim 3, further including a stent graft within the pocket defined by the flexible sheet.

6. The stent graft loading system of claim 5, wherein the stent graft includes a luminal graft component having a proximal end and a distal end, the stent graft including a crown stent fixed to the proximal end of the luminal graft component, and a clasping stent fixed to and within the luminal graft component, the clasping stent being distal to the crown stent and adjacent to the crown stent, the clasping stent including at least one bare apex that is exposed to the lumen of the luminal graft component, and releasably fixable to the apex clasping component.

7. The stent graft loading system of claim 6, wherein the proximal clasping component includes prongs that extend distally from the proximal clasping component and are mateable with the distal clasping component, whereby the at least one apex of the clasping stent can be captured between the prongs of the proximal clasping component and the distal clasping component, and wherein the at least one apex is released by proximal movement of the apex clasping catheter.

8. The stent graft loading system of claim 7, wherein the stent graft includes at least one suture loop at a proximal end of the stent graft and within the stent graft, and wherein at least one support wire is fixed to and extends distally from the apex capture catheter, the at least one support wire being threaded through the at least one suture loop.

9. The stent graft loading system of claim 3, wherein the stent graft includes a support bar, and wherein the support bar of the stent graft is diametrically opposed to the slot of the rigid cylinder.

10. The stent graft loading system of claim 9, wherein the guidewire catheter is curved, and the support bar of the stent graft is at a superior portion of the curvature of the apex capture catheter and to the slot of the rigid cylinder.

11. A method of loading a stent graft into a stent graft delivery device, comprising the steps of:

a) loading a stent graft into a pocket defined by a flexible sheet having a straight edge and a second edge opposite the straight edge, wherein the straight edge has a raised component that extends parallel to and is adjacent a slot defined by a rigid cylinder, and extending parallel to a longitudinal axis of the rigid cylinder, the flexible sheet extending from the raised component of the straight edge through the slot and into a lumen defined by the rigid cylinder, and from within the lumen through the slot to the opposite edge of the flexible sheet outside of the rigid cylinder to thereby define the pocket of the flexible sheet;

b) pulling the second edge of the flexible sheet away from the rigid cylinder, thereby reducing the volume of the pocket and radially constricting the stent graft and causing a longitudinal axis of the stent graft to move away from the longitudinal axis of the rigid cylinder and toward the slot of the rigid cylinder; and c) directing the stent graft, while it is radially constricted thereby forming a radially constricted stent graft, along its longitudinal axis from the pocket through an opening defined by a block and into a loading tube, while remaining radially constricted along its longitudinal axis.

12. The method of claim 11, wherein the step of directing the stent graft, while it is radially constricted, from the pocket includes directing the radially constricted stent graft through an opening at a block at one end of the rigid cylinder.

13. The method of claim 12, wherein the opening defined by the block has a diameter less than that of the pocket prior to radially constricting the pocket and the stent graft, and wherein the block is beveled at a circumference of the opening.

14. The method of claim 12, wherein the loading tube is intermediate to a stent graft delivery device, whereby the radially constricted stent graft is directed from the radially-constricted member to the stent graft delivery device along the longitudinal axis of the radially constricted stent graft while radially constricted.

15. The method of claim 14, further including the step of clasping at least one proximal apex of a clasping stent of the stent graft to an apex-clasping component of a stent graft delivery device prior to constricting the stent graft within the pocket of the flexible sheet.

16. The method of claim 15, further including the step of releasing the clasping stent of the radially constricted stent graft from the pocket before clamping the proximal apex of the clasping stent to the apex-clasping component of the stent graft delivery device, and then redirecting the radially constricted stent graft back into the pocket.

17. The method of claim 16, further including the step of threading at least one support wire of the stent graft delivery device through a suture of the stent graft prior to radially constricting the stent graft.

18. The method of claim 17, further including the step of applying a clamp to the threaded suture prior to radially constricting the stent graft.

19. The method of claim 18, further including the step of screw-loading a rod onto threads at a distal end of the guidewire catheter.

20. The method of claim 19, wherein the stent graft includes a support bar, and wherein the support bar of the stent graft is oriented during loading into the pocket radially opposite to the longitudinal slot of the rigid cylinder.

* * * * *